United States Patent [19]

Verbrugge et al.

[11] 4,180,520

[45] Dec. 25, 1979

[54] PREPARATION OF NITRILES

[75] Inventors: Pieter A. Verbrugge; Petrus A. Kramer, both of Amsterdam, Netherlands

[73] Assignee: Shell Oil Company, Houston, Tex.

[21] Appl. No.: 939,749

[22] Filed: Sep. 5, 1978

Related U.S. Application Data

[62] Division of Ser. No. 806,034, Jun. 13, 1977, Pat. No. 4,132,728.

[30] Foreign Application Priority Data

Aug. 16, 1976 [GB] United Kingdom ............... 33969/76
Aug. 16, 1976 [GB] United Kingdom ............... 33970/76

[51] Int. Cl.$^2$ ................... C07C 121/16; C07C 121/66

[52] U.S. Cl. ................................ 260/465 R; 260/464; 260/465 G; 260/465 K; 260/465.1

[58] Field of Search ............. 260/465 R, 465 G, 465.1

[56] References Cited

PUBLICATIONS

Profitt et al., J. Org. Chem., vol. 40, No. 1, pp. 127–128 (1975).

*Primary Examiner*—Dolph H. Torrence

[57] ABSTRACT

α,β-Unsaturated nitriles are prepared from carbonyl compounds and then reduced by reaction with an alkanol and magnesium in the presence of an ammonium salt.

14 Claims, No Drawings

PREPARATION OF NITRILES

This is a division, of application Ser. No. 806,034, filed June 13, 1977 now U.S. Pat. No. 4,132,728.

BACKGROUND OF THE INVENTION

1. Field of the Invention

The invention relates to an improved process for preparation and reduction of $\alpha,\beta$-unsaturated nitriles.

2. Description of the Prior Art

Bull. Soc. Chim. France 1963, pp. 677–681 shows that $\beta,\beta$-dimethyl-$\alpha$-cyanostyrene can be prepared in 30% yield by refluxing 0.3 mol of benzyl cyanide, 1.3 mol of acetone and 10 ml 3 N methanolic KOH for two hours, followed by cooling, neutralizing, drying and distilling. This publication also shows that $\beta$-methyl-$\alpha$-cyanostyrene is obtained in 47% yield by heating 0.25 mol of benzyl cyanide, 1 mol of acetaldehyde and 2 ml 3 N methanolic KOH until the mixture becomes cloudy (about 65° C.), followed by cooling, neutralizing, drying and distilling. Applicant has found that further stirring under reflux does not increase these low yields. The molar ratios of KOH to benzyl cyanide in these two experiments were 0.10 and 0.024, respectively.

J. Org. Chem. 40 (1975) 127–128 shows that alpha,beta-ethylenically unsaturated nitriles can be hydrogenated to give a high yield of the corresponding saturated nitriles by reaction with methanol and magnesium, followed by acidification of the reaction mixture obtained. In a typical experimental procedure a starting amount of the unsaturated nitrile of 0.1 mol/l methanol was used. The use of such highly dilute solutions is not very attractive for a commercial process. Applicant has tried to use more concentrated solutions but has found that in such a case the reaction with methanol and magnesium comes to a standstill at a moment when a considerable part of the alpha,beta-ethylenically unsaturated nitrile is still unconverted.

It has now been found that an increase in the molar ratio of KOH to benzyl cyanide considerably enhances the yield of $\alpha,\beta$-unsaturated nitriles and that the presence of certain salts promotes their hydrogenation.

SUMMARY OF THE INVENTION

Accordingly the invention may be defined as relating to a process for the preparation of a nitrile of the general formula

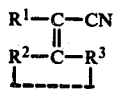
(I)

wherein R$^1$ represents an optionally substituted aryl group, R$^2$ is optionally substituted hydrocarbyl group and R$^3$ an optionally substituted hydrocarbyl group or a hydrogen atom, or, alternatively, R$^2$ and R$^3$ together with the carbon atom to which they are attached form a carbocyclic group, as indicated by the dotted line, which comprises reacting a nitrile of the general formula

 (II)

wherein R$^1$ has the same meaning as in the general formula I, with a carbonyl compound of the general formula

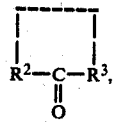
III wherein R$^2$ and R$^3$ have the same meaning as in the general formula I, in the presence of an alkanol and a hydroxide of an alkali metal having an atomic number of at least 11, using a molar ratio of the hydroxide to the compound of the general formula II of at least 0.15.

The molar ratio of the alkali metal hydroxide to the compound of the general formula II must be at least 0.15 to ensure an enhanced yield of the compounds of the general formula I. This molar ratio is preferably in the range of from 0.2 to 0.8; molar ratios increasing above 0.8 usually offer no additional advantages. Preferred molar ratios are usually in the range of from 0.3 to 0.6.

R$^1$ in the general formula I may be a carbocyclic or a heterocyclic aryl groups. Examples of carbocyclic aryl groups are phenyl, 1-napthyl, 2-naphthyl and 2-anthryl groups. Heterocyclic aromatic groups are derived from hetero-aromatic compounds which are defined as in Kirk-Othmer, "Encyclopedia of Chemical Technology," Second Edition, Volume 2 (1963), page 702: obtained by replacement of one or more carbon atoms of a carbocyclic aromatic compound by a heteroatom—for example pyridine, pyrimidine, pyrazine, quinoline and isoquinoline—and these heteroaromatic compounds also include those heterocyclic compounds having five-membered rings which show aromatic characteristics and are mentioned on page 703 of said volume, for example thiophene, pyrrole, furan, indole and benzothiophene. Examples of substituents which may be present in R$^1$ are one or more alkyl or alkoxy groups in which the alkyl portion contains from 1 to 4 carbon atoms or halogen atoms having an atomic number of from 9 to 35, inclusive. Very high yields of compounds of the general formula I are usually obtained when R$^1$ represents an optionally substituted aryl group of up to 12 carbon atoms, e.g., an optionally substituted phenyl group, particularly a 4-chlorophenyl group.

Preferred alkanols are those having less than ten carbon atoms per molecule. The alkanol may have a straight or a branched carbon chain. Methanol, ethanol, 1-propanol, 2-propanol and the butanols are particularly preferred. Methanol is the most preferred of these alcohols, because it usually affords the compounds of the general formula I in the highest yield after the same reaction time.

Among the alkali metal hydroxides—i.e., the hydroxides of sodium, potassium, rubidium and cesium—potassium hydroxide is preferred, because it usually affords the compounds of the general formula I in a higher yield than sodium hydroxide after the same reaction time and because it is less expensive than the hydroxides of rubidium and cesium. If desired, the alkali metal hydroxide may be formed in situ, for example by starting from the corresponding alkali metal oxide.

The hydrocarbyl groups represented by R$^2$ and R$^3$ in the general formula I may be, for example, an alkyl, a cycloalkyl or an aryl group of up to 20 carbon atoms or one of these which is substituted by another one of these three groups. If desired the hydrocarbyl groups may be substituted by non-hydrocarbyl groups, for example by an alkoxy group. The alkyl and cycloalkyl groups may be saturated or unsaturated. Very good results have been obtained with compounds in which $R^2$ and $R^3$ stand for alkyl groups of 1 to 6 carbon atoms. Examples of ketones of the general formula III which may be used are acetone, 2-butanone, 2-pentanone, 4-methyl-3-pentene-2-one, acetophenone and 1'-butyronaphthone. Acetone is particularly preferred. Examples of aldehydes of the general formula III are propanal, butanal and hexanal. Examples of compounds of the general formula III wherein $R^2$ and $R^3$ together with the carbon atom to which they are attached form a carbocyclic group of 4 to 12 ring carbon atoms, e.g., cyclobutanone, cyclopentanone, cyclohexanone and cyclododecanone. The carbocyclic group may contain unsaturated carbon-carbon bonds, as is the case in, for example, 2-cyclohexene-1-one and methyl derivatives thereof.

The compounds of the general formulas III and II are preferably used in a molar ratio of III to II of at least 1; low yields of nitriles of the general formula I are obtained at molar ratios below 1. This molar ratio is preferably in the range of from 1.5 to 10 and particularly of from 2 to 5.

The molar ratio of alkanol to alkali metal hydroxide can vary between wide limits and is usually between 1 and 20.

The compounds of the general formula I are usually obtained in a low yield—after a long time—at temperatures below 50° C.; temperatures in the range of from 50° to 100° C. are usually very suitable. Temperatures higher than 100° C. may be used, if desired.

The process may be conducted in the presence of a solid water-binding agent, for example of calcium oxide, sodium carbonate or potassium carbonate.

The process may be carried out by stirring a mixture of the nitrile of the general formula II, the carbonyl compound of the general formula III and the alkanol and adding the alkali metal hydroxide to the stirred mixture. Then, the mixture is heated for a certain time. The nitrile of the general formula I may be isolated from the reaction mixture thus obtained by flashing off carbonyl compound of the general formula III, dissolving the organic material of the residue in an organic solvent such as petroleum ether or toluene, removing alkali metal hydroxide by washing the water until the used washing water has a pH of about 7, drying the washed solution and subjecting the dried solution to fractional distillation.

The invention also relates to a process for the preparation of a nitrile of formula IV

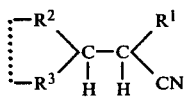   IV wherein $R^1$ represents an optionally substituted hydrocarbyl group or a hydrogen atom, and $R^2$ and $R^3$ each represents an optionally substituted hydrocarbyl group or a hydrogen atom, or, alternatively, $R^2$ and $R^3$ together with the carbon atom to which they are attached form a carbocyclic group, as indicated by the dotted line, which comprises reacting a nitrile of formula

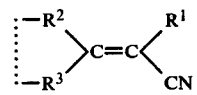   I wherein $R^1$, $R^2$ and $R^3$ are hydrogen or have the same meaning as given for formula IV below or for formula I on pages 3–5 of the specification, with an alkanol containing 1 to 4 carbon atoms and magnesium in the presence of an ammonium salt.

The hydrocarbyl groups $R^1$, $R^2$ and $R^3$ may represent, for example, substituted or unsubstituted alkyl or cycloalkyl groups or aryl groups of up to 20 carbon atoms. The substituents should not react with the compounds involved in the process according to the present invention. Examples of substituents are one or more halogen atoms having an atomic number of from 9 to 35, inclusive, and alkyl and alkoxy groups in which the alkyl portion contains from 1 to 4 carbon atoms. If desired, the alkyl and cycloalkyl groups may have an ethylenically unsaturated carbon-carbon bond; this bond may be conjugated with the double bond in the compound of formula I. Very good results have been obtained with compounds in which $R^1$ represents an optionally substituted aryl group of up to 12 carbon atoms and $R^2$ and $R^3$ stand for alkyl groups each containing 1 to 6 carbon atoms. The aryl group may be carbocyclic or heterocyclic. Examples of carbocyclic and heterocyclic aromatic groups are given on pages 3 and 4 of the specification. As an aryl group an optionally substituted phenyl group is very suitable. Examples of alkyl groups represented by $R^2$ and $R^3$ are methyl, ethyl, n-propyl, isopropyl, isobutyl and sec-butyl groups. Very good results have been obtained with 2-(4-chlorophenyl)-3-methyl-2-butenenitrile. $R^2$ and $R^3$ in formula I may be part of, for example, an optionally substituted cycloalkylidene ring of 4 to 12 ring carbon atoms, e.g., cyclobutylidene, cyclopentylidene, cyclohexylidene or cyclododecylidene group.

The reaction of the nitrile of the general formula I with magnesium and the alkanol is caused to continue even when a very low molar ratio of the ammonium salt to magnesium is used, for example of at least 0.002. The most suitable molar ratios of ammonium salt to magnesium are usually in the range of from 0.01 to 2.

The alkanols which can be used contain from 1 to 4 carbon atoms, e.g., methanol and ethanol. Methanol is preferred, because the best effect on the reaction is obtained in the very low range of from 0.01 to 0.1 for the molar ratio of ammonium salt to magnesium. For ethanol, this range is usually of from 1 to 2. Moreover, in these ranges the nitriles of formula IV are often obtained in quantitative yield. The use of a mixture of methanol and ethanol is not precluded.

Examples of ammonium salts which may be used are organic or inorganic salts, preferably inorganic salts such as ammonium chloride, ammonium bromide, ammonium phosphate and ammonium sulphate. Ammonium halides are preferred, especially ammonium chloride.

The invention allows the use of starting amounts of the nitrile of formula I of at least 0.5 mole/l alkanol and often of at least 4 mol/l alkanol, which is attractive for a commercial process. Usually, this amount of nitrile is not higher than 6 mol/l alkanol.

The molar ratio of magnesium to the nitrile of formula I is suitably at least 1, preferably in the range of from 1 to 5 and particularly of from 1 to 2. Molar ratios higher than 5 are not precluded.

When the process is conducted at temperatures above 30° C. hydrogen may escape from the reaction mixture, which may reduce the yield of the nitrile of the general formula IV, in view of this the process is preferably carried out at a temperature not higher than 30° C.; temperatures above 30° C., however, are not precluded. Preferred temperatures are in the range of from 0° C. to 30° C. and in particular of from 15° C. to 30° C.

The process may be carried out by agitating, e.g., stirring, the nitrile of formula I with the alkanol, magnesium and the ammonium salt. The nitrile of formula IV may be isolated from the reaction mixture by acidification—for example by addition of an acidic aqueous solution such as hydrochloric acid or aqueous sulphuric acid, or of gaseous hydrogen chloride—, flashing off the alkanol, extracting the residue with an organic solvent and distilling the extract phase. Alternatively, the nitrile is isolated by adding sufficient ammonium salt to the reaction mixture to obtain only water-soluble magnesium compounds, flashing off the alkanol, extracting the residue with an organic solvent, washing the extract phase with water, drying the washed liquid and distilling the dried liquid.

After preparation of the unsaturated nitrile and before reduction, any excess of carbonyl compound of the general formula III is flashed off, the residue is washed with water to remove alkali metal hydroxide and the washed liquid is dried. Then, magnesium, alkanol and ammonium salt are added to the dried liquid to effect formation of the nitrile of the general formula IV according to the present invention. The presence of an alkali metal hydroxide counteracts the reaction of the nitrile of the general formula I with the alkanol and magnesium, but some alkali metal hydroxide may be present in the dried liquid, because it is converted by part of the ammonium salt into alkali metal salt, ammonia and water.

Nitriles of the general formula I may be converted into the corresponding amides by replacing the cyano group by a carbamoyl group in a known manner. The carboxamides thus obtained may be converted in a known manner into the corresponding carboxylic acids.

Compounds of formula IV are valuable intermediates, particularly for the preparation of pesticides, such as esters of 2-(4-chlorophenyl)-3-methylbutanoic acid, which are valuable insecticides such as those disclosed in U.S. Pat. No. 3,996,244. The examples further illustrate the invention.

EXAMPLE I

A flask was charged with 0.2 mol of 4-chloro-benzyl cyanide, 0.57 mol (42 ml) of acetone, 0.27 mol (11 ml) of methanol and 0.09 mol of potassium hydroxide in pellets containing 15%w of water, the molar ratios of KOH to 4-chlorobenzyl cyanide and of acetone to 4-chlorobenzyl cyanide being 0.45 and 2.85, respectively. The contents of the flask were stirred and boiled for ten minutes under reflux at atmospheric pressure. Then, acetone and methanol were flashed off, the organic material in the residue was dissolved in 60 ml of toluene and potassium hydroxide was removed by washing the solution with two 20-ml portions of water. The washed solution was dried over anhydrous magnesium sulphate, the magnesium sulphate was removed by filtration and the toluene was flashed off, leaving a yellow orange liquid residue (41.8 g) containing 2-(4-chlorophenyl)-3-methyl-2-butenenitrile in an amount corresponding to a yield of more than 95%, calculated on starting 4-chlorobenzyl cyanide. The conversion of 4-chlorobenzyl cyanide was 100%.

EXAMPLE II

The experiment of Example I was repeated, but this time 0.15 mol of NaOH in pellets was used instead of 0.09 mol of KOH pellets, the molar ratio of NaOH to 4-chlorobenzyl cyanide being 0.75. 2-(4-chlorophenyl)-3-methyl-2-butenenitrile was formed in a yield of more than 95% after a reaction time of 32 minutes.

EXAMPLE III

The experiment of Example I was repeated, but this time 0.285 mol instead of 0.57 mol of acetone was used, the molar ratio of acetone to 4-chlorobenzyl cyanide being 1.425, and the contents of the flask were stirred for fifteen instead of ten minutes. The conversion of 4-chlorobenzyl cyanide was 100% and the yield of 2-(4-chlorophenyl)-3-methyl-2-butenenitrile was 80%, calculated on starting 4-chlorobenzyl cyanide.

EXAMPLE IV

The experiment of Example I was repeated, but this time 0.045 mol instead of 0.09 mol of potassium hydroxide was used, the molar ratio of KOH to 4-chlorobenzyl cyanide being 0.225, and the contents of the flask were stirred for 55 instead of 10 minutes. It was found that 70% of the 4-chlorobenzyl cyanide had been converted, mainly to 2-(4-chlorophenyl)-3-methyl-2-butenenitrile. Further stirring did not increase the conversion.

EXAMPLE V

The experiment of Example I was repeated, but this time 11 ml of 2-propanol instead of 11 ml of methanol was used and the contents of the flask were stirred under reflux for 30 instead of 10 minutes. The conversion of 4-chlorobenzyl cyanide was 100% and the yield of 2-(4-chlorophenyl)-3-methyl-2-butenenitrile was more than 95%, calculated on starting 4-chlorobenzyl cyanide.

EXAMPLES VI–XII

A flask was charged with 5 g of an arylacetonitrile, 10 ml of a carbonyl compound, 2 ml of methanol and 1 g of KOH pellets. Seven experiments were conducted as described in Example I. The arylacetonitriles and carbonyl compounds used and the reaction times adopted are stated in the Table. The Table also presents the names of the nitriles formed and their yields, calculated on starting arylacetonitrile. The nitriles formed in the Examples IX, X, XI and XII are novel.

Table

| Example No. | nitrile | Carbonyl compound | Molar ratio of KOH to arylacetonitrile | Molar ratio of Carbonyl compound to arylacetonitrile | Reaction time, min. | Nitrile formed Name | Yield, % |
|---|---|---|---|---|---|---|---|
| VI | benzyl cyanide | acetone | 0.35 | 3.2 | 15 | 3-methyl-2-phenyl-2-butenenitrile | 80 |
| VII | " | 2-butanone | 0.35 | 2.6 | 38 | 3-methyl-2-phenyl-2- | 100 |

| Example No. | nitrile | Carbonyl compound | Molar ratio of KOH to aryl-acetonitrile | Molar ratio of Carbonyl compound to arylacetonitrile | Reaction time, min. | Nitrile formed Name | Yield, % |
|---|---|---|---|---|---|---|---|
| VIII | " | n-butanal | 0.35 | 2.6 | 10 | pentenenitrile 2-phenyl-2-hexene-nitrile | 100 |
| IX | p-chlorobenzyl cyanide | 4-methyl-3-pen-tene-2-one | 0.35 | 2.0 | 8 | 2-(4-chlorophenyl)-3,5-dimethyl-2,4-hexadienenitrile | 30 |
| X | 1-naphthyl cyanide | acetone | 0.51 | 4.5 | 20 | 3-methyl-2-(1-naphthyl)-2-butenenitrile | 70 |
| XI | 4-methylbenzyl cyanide | " | 0.40 | 3.6 | 22 | 3-methyl-2-(4-methyl-phenyl)-2-butenenitrile | 80 |
| XII | 3,5-dimethyl-benzyl cyanide | " | 0.45 | 4.0 | 20 | 2-(3,5-dimethylphenyl)-3-methyl-2-buteneni-trile | 60 |

The nuclear magnetic resonance spectrum of the novel nitrile formed in Example IX measured at 60 MHz in deuterochloroform solution showed the following absorptions relative to a tetramethylsilane standard: $\delta = 1.73$ ppm (singlet, two CH$_3$); $\delta = 1.82$ ppm (doublet, one CH$_3$); $\delta = 6.03$ ppm (multiplet, =CH); $\delta = 7.30$ ppm (singlet, four H bound to aromatic nucleus). The E and Z structures were both present.

Analysis of the residues obtained in the Examples X, XI and XII by means of infrared spectrography yielded the following absorptions (wave length in micron):
Example X: 4.56; 12.47; 12.87.
Example XI: 4.56; 12.20; 12.25.
Example XII: 4.55; 11.77; 14.25.

EXAMPLE XIII

The experiment of Example VI was repeated, but this time 1 g of sodium hydroxide was used instead of 1 g of KOH pellets, the molar ratio of NaOH to benzyl cyanide being 0.58. 3-Methyl-2-phenyl-2-butenenitrile was formed in a yield of 60% after a reaction time of 17 minutes.

EXAMPLE XIV

A flask was charged with 0.033 mol of 4-chlorobenzyl cyanide, 0.057 mol of cyclobutanone, 0.05 mol (2 ml) of methanol and 0.015 mol of KOH in pellets containing 15%w of water, the molar ratios of KOH to 4-chlorobenzyl cyanide and of cyclobutanone to 4-chlorobenzyl cyanide being 0.45 and 1.73, respectively. The contents of the flask were stirred and boiled for five minutes under reflux at atmospheric pressure. The reaction mixture was taken up in diethyl ether, the etherial solution was washed with water until the washing water had a pH of 7, the washed solution was dried in the presence of anhydrous magnesium sulphate and the dried solution was boiled down at subatmospheric pressure. The residue (6.25 g) showed the following infrared absorptions (in micron), indicating the presence of the novel compound 2-(4-chlorophenyl)-2-cyclobutyl-ideneethanenitrile: 3.0; 3.40; 3.47; 3.54; 4.50; 4.56; 5.30; 5.70; 6.10; 6.30; 6.75; 6.96; 7.14; 8.0; 9.20; 9.90; 11.10; 11.42; 11.66; 12.10; 12.58; 13.70; 14.34.

EXAMPLE XV

The experiment of Example XIV was repeated, but this time 0.57 mol of 3,5,5-trimethyl-2-cyclohexen-1-one was used instead of cyclobutanone. The residue contained the novel compound 2-(4-chlorophenyl)-2-(3,5,5-trimethyl-2-cyclohexylidene)ethanenitrile.

The NMR spectrum of this novel compound measured at 60 MHz in deuterochloroform solution showed the following absorptions relative to a tetramethylsilane standard (the E and Z structures were both present):
$\delta = 0.86$ and 1.02 ppm (two singlets, geminal CH$_3$);
$\delta = 1.81$ and 1.93 ppm (two singlets, one CH$_3$ bound to =C);
$\delta = 2.04$–2.08–2.23–2.52 ppm (CH$_2$ ring protons);
$\delta = 6.18$ and 6.63 ppm (two singlets, =CH);
$\delta = 7.31$ ppm (singlet, four H bound to aromatic nucleus).

The experiments described in the following Examples XVI–XIX were conducted in a flask provided with a magnetic stirrer, a thermometer and a reflux condensor. With the exception of Example XVI, the reaction mixture was worked up by adding 36%w aqueous hydrochloric acid until all the magnesium had been converted into the chloride, flashing off the methanol, taking up the residue in petroleum ether having a boiling range at atmospheric pressure between 60° and 80° C., removing the solid hydrated magnesium chloride by filtration and boiling down the filtrate at subatmospheric pressure. The residue was analyzed by infrared spectroscopy, analysis of the nuclear magnetic resonance spectrum and gas-liquid chromatography. The starting and product nitriles were 2-(4-chlorophenyl)-3-methyl-2-butenenitrile and 2-(4-chlorophenyl)-3-methylbutanenitrile, to be called hereinafter nitriles A and B, respectively. The yields of nitrile B are calculated on starting nitrile A.

Experiment XVI not according to the invention

The flask was charged with 100 mmol of nitrile A, 24 ml of methanol and 107 mmol of magnesium curlings, the amount of nitrile A in methanol and the molar ratio of magnesium to nitrile A being 4.2 mol/l methanol and 1.07, respectively. The reaction came to a standstill at 60% conversion of nitrile A.

EXAMPLE XVI

The flask was charged with 100 mmol of nitrile A, 24 ml of methanol, 107 mmol of magnesium curlings and 114 mmol of ammonium chloride, the amount of nitrile A in methanol, the molar ratio of magnesium to nitrile A and of ammonium chloride to magnesium being 4.2 mol/l methanol, 1.07 and 1.07, respectively. After 5 hours' stirring at 29° C. the magnesium had disappeared. Nitrile B was isolated from the reaction mixture by adding an additional quantity of 190 mmol of ammonium chloride, flashing off the methanol, mixing the residue with petroleum ether having a boiling range at atmospheric pressure between 60° and 80° C., washing away the inorganic material with water, drying the washed liquid in the presence of anhydrous magnesium sulphate and boiling down the dried liquid at subatmospheric pressure. Nitrile B was obtained in quantitative yield.

EXAMPLE XVII

The flask was charged with 235 mmol of nitrile A, 88 ml of methanol, 296 mmol of magnesium curlings and 19 mmol of ammonium chloride, the amount of nitrile A in methanol, the molar ratio of magnesium to nitrile A and of ammonium chloride to magnesium being 4.2 mol/l methanol, 1.26 and 0.06, respectively. After 5 hours stirring at 29° C. the magnesium had disappeared. Nitrile B was obtained in quantitative yield.

Experiment XVII not according to the invention

The experiment of Example XVII was repeated, but in this case the ammonium chloride was omitted. The reaction came to a standstill after two hours' stirring. Analysis of the residue obtained after working up showed the conversion of nitrile A to be 60% and the yield of nitrile B to be 60%.

EXAMPLE XVIII

The flask was charged with 23.5 mmol of nitrile A, 25 ml of ethanol, 41.1 mmol of magnesium curlings and 56.1 mmol of ammonium chloride, the amount of nitrile A in ethanol and the molar ratios of magnesium to nitrile A and of ammonium chloride to magnesium being 0.94 mol/l ethanol, 1.75, and 1.36, respectively. After 5 hours stirring at 29° C. the magnesium had disappeared. Nitrile B was obtained in quantitative yield.

Experiment XVIII not according to the invention

The experiment of Example XVIII was repeated, but in this case the ammonium chloride was omitted. No reaction was observed.

EXAMPLE XIX

The flask was charged with 5.2 mmol of nitrile A, 9.3 ml of methanol, 41.2 mmol of magnesium curlings and 2.3 mmol of KOH, the amount of nitrile A in methanol and the molar ratio of magnesium to nitrile A being 0.6 mol/l methanol and 7.9, respectively. No reaction had taken place after two hours stirring at 29° C. Then, 5 mmol of ammonium chloride was added, the molar ratio of ammonium chloride to magnesium, after reaction of 2.3 mmol of ammonium chloride with KOH, being 0.07. Ammonia was developed and the reaction started immediately. After one hour stirring the magnesium had disappeared and nitrile B was obtained in quantitative yield.

We claim:

1. A process for the preparation of a nitrile of formula IV

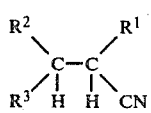

wherein $R^1$ represents an aryl group containing up to 12 carbon atoms or a hydrogen atom, and $R^2$ and $R^3$ each represents an alkyl group containing from 1 to 6 carbon atoms or a hydrogen atom, which process comprises reacting a nitrile of formula I

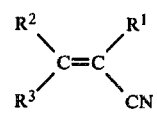

wherein $R^1$, $R^2$ and $R^3$ have the same meaning as in formula IV with an alkanol containing from 1 to 4 carbon atoms and magnesium in the presence of an ammonium salt in a molar ratio of ammonium salt to magnesium of at least 0.002.

2. A process according to claim 1, in which the molar ratio of ammonium salt to magnesium is in the range of from 0.01 to 2.

3. A process according to claim 1, in which the alkanol is methanol.

4. A process according to claim 3, in which the molar ratio of ammonium salt to magnesium is in the range of from 0.01 to 0.1.

5. A process according to claim 1, in which the alkanol is ethanol.

6. A process according to claim 5, in which the molar ratio of ammonium salt to magnesium is in the range of from 1 to 2.

7. A process according to claim 1, in which the ammonium salt is ammonium chloride.

8. A process according to claim 1, in which the nitrile of formula I is used in a starting amount of at least 0.5 mol/l alkanol.

9. A process according to claim 8, in which the nitrile of formula I is used in a starting amount between 4 and 6 mol/l alkanol.

10. A process according to claim 1, in which the molar ratio of magnesium to the nitrile of formula I is in the range of from 1 to 5.

11. A process according to claim 10, in which the molar ratio of magnesium to the nitrile of formula I is in the range of from 1 to 2.

12. A process according to claim 1, which is conducted at a temperature in the range of from 0° C. to 30° C.

13. A process according to claim 1, in which the nitrile of formula I is 2-(4-chlorophenyl)-3-methyl-2-butenenitrile.

14. A process according to claim 1, in which the nitrile of formula I has been obtained by reacting a nitrile of formula II $$R^1—CH_2CN \qquad II$$

wherein $R^1$ represents an aryl group just as $R^1$ in formula I, with a carbonyl compound of formula III

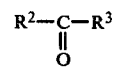

wherein $R^2$ and $R^3$ have the same meaning as in formula I in the presence of an alkanol and a hydroxide of an alkali metal having an atomic number of at least 11 using a molar ratio of the hydroxide to the compound of formula II of at least 0.15, followed by removal of excess of carbonyl compound of formula III, if any, washing of the residue with water and drying of the washed residue.

* * * * *